(12) United States Patent
Chang et al.

(10) Patent No.: US 10,422,744 B2
(45) Date of Patent: Sep. 24, 2019

(54) INTERFEROMETER AND IMAGING METHOD THEREFOR

(71) Applicant: INDUSTRIAL TECHNOLOGY RESEARCH INSTITUTE, Hsinchu (TW)

(72) Inventors: Ting-Wei Chang, New Taipei (TW); Yuan-Chin Lee, Hsinchu (TW); Chi-Shen Chang, Zhubei (TW); Hung-Chih Chiang, Chiayi (TW); Shuen-Chen Chen, Taichung (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 0 days.

(21) Appl. No.: 15/723,796

(22) Filed: Oct. 3, 2017

(65) Prior Publication Data

US 2018/0095033 A1    Apr. 5, 2018

Related U.S. Application Data

(60) Provisional application No. 62/403,761, filed on Oct. 4, 2016.

(30) Foreign Application Priority Data

Aug. 15, 2017  (TW) .............................. 106127569 A

(51) Int. Cl.
*G01N 21/45* (2006.01)
*G01B 9/00* (2006.01)
(Continued)

(52) U.S. Cl.
CPC .............. *G01N 21/45* (2013.01); *G01B 9/00* (2013.01); *G01N 21/4795* (2013.01); *G01N 2021/1787* (2013.01)

(58) Field of Classification Search
CPC .... G01N 21/45; G01N 21/47; G01B 11/2441; G01B 9/02072; G01D 5/266
(Continued)

(56) References Cited

U.S. PATENT DOCUMENTS 2,657,373 A * 10/1953 Piety ......................... G01V 1/16
367/58
6,005,952 A * 12/1999 Klippel ................ G10K 11/178
381/71.11
(Continued)

FOREIGN PATENT DOCUMENTS

CN         2452005 Y      10/2001
CN         1320812 A      11/2001
(Continued)

OTHER PUBLICATIONS

Bhaduri et al., "Derivative method for phase retrieval in off-axis quantitative phase imaging", Optics Letters, Jun. 1, 2012, vol. 37, No. 11, pp. 1868-1870.
(Continued)

*Primary Examiner* — Mohamed K Amara
(74) *Attorney, Agent, or Firm* — Birch, Stewart, Kolasch & Birch, LLP

(57) ABSTRACT

Provided is an interferometer for inspecting a test sample. The interferometer includes: a light source for providing a light beam; a beam splitting element, splitting the light beam into first and second incident light, wherein the first incident light is reflected by the test sample into first reflection light; a reflecting element, reflecting the second incident light into second reflection light; an optical detection element, receiving the first and the second reflection light into an interference signal; and a signal processing module, coupled to the optical detection element, for performing spatial differential
(Continued)

calculation on the interference signal to generate a demodulation image of the test sample.

6 Claims, 3 Drawing Sheets

(51) Int. Cl.
G01N 21/47 (2006.01)
G01N 21/17 (2006.01)

(58) Field of Classification Search
USPC .......................................................... 356/497
See application file for complete search history.

(56) References Cited

U.S. PATENT DOCUMENTS

| | | | |
|---|---|---|---|
| 6,847,459 B2 | 1/2005 | Zhu et al. | |
| 7,088,454 B2 | 8/2006 | Chang et al. | |
| 7,918,791 B2 | 4/2011 | Lu et al. | |
| 7,962,198 B2 | 6/2011 | Pogue et al. | |
| 8,165,383 B2 | 4/2012 | Faivishevsky | |
| 8,559,016 B2* | 10/2013 | Nebosis | G01N 21/4795 356/497 |
| 8,693,745 B2 | 4/2014 | Izatt et al. | |
| 8,855,265 B2* | 10/2014 | Engel | A61B 6/00 378/36 |
| 8,873,034 B2 | 10/2014 | Lin et al. | |
| 9,019,479 B2* | 4/2015 | Nagai | A61B 6/00 356/4.09 |
| 9,185,357 B2 | 11/2015 | Boccara et al. | |
| 2003/0117894 A1* | 6/2003 | Curtis | G01V 1/20 367/58 |
| 2005/0146727 A1* | 7/2005 | Hill | G01B 9/02019 356/498 |
| 2005/0146730 A1* | 7/2005 | Endo | G01D 11/26 356/512 |
| 2007/0091769 A1* | 4/2007 | Yamakage | G11B 7/00772 369/103 |
| 2008/0285043 A1* | 11/2008 | Fercher | A61B 3/102 356/451 |
| 2010/0110846 A1* | 5/2010 | Park | G11B 7/0065 369/44.23 |
| 2011/0061860 A1* | 3/2011 | Dean | E21B 43/00 166/250.01 |
| 2011/0166693 A1* | 7/2011 | Nishibashi | G05B 19/4103 700/187 |
| 2013/0038462 A1* | 2/2013 | Abdi | H04B 11/00 340/850 |
| 2013/0237825 A1* | 9/2013 | Sasaki | A61B 8/5269 600/443 |
| 2013/0259152 A1* | 10/2013 | Simon | H04L 27/00 375/295 |
| 2013/0265558 A1* | 10/2013 | Harayama | G03F 7/70591 355/52 |
| 2014/0064351 A1* | 3/2014 | Hidaka | H04L 27/01 375/232 |
| 2015/0248109 A1* | 9/2015 | Mathuis | G03H 1/0443 359/370 |
| 2016/0061725 A1 | 3/2016 | Choi et al. | |
| 2017/0017134 A1* | 1/2017 | Cho | G03B 9/02 |
| 2017/0176614 A1* | 6/2017 | Alhukail | G01V 1/30 |
| 2017/0193659 A1 | 7/2017 | Wang et al. | |
| 2017/0205222 A1* | 7/2017 | Mathuis | G01B 9/02047 |
| 2017/0277293 A1* | 9/2017 | Ling | G06F 3/044 |

FOREIGN PATENT DOCUMENTS

| | | | | |
|---|---|---|---|---|
| CN | 1328637 A | 12/2001 | | |
| CN | 101243298 A | 8/2008 | | |
| CN | 101527619 B | 6/2014 | | |
| CN | 105050483 A | 11/2015 | | |
| JP | 2013102951 A | * | 5/2013 | ............... A61B 6/00 |
| TW | 200739033 A | 10/2007 | | |
| TW | I385598 B1 | 2/2013 | | |
| TW | I414818 B | 11/2013 | | |
| TW | I453523 B | 9/2014 | | |
| TW | I463177 B | 12/2014 | | |
| TW | 201617581 A | 5/2016 | | |
| TW | I553294 B | 10/2016 | | |
| WO | WO 2006/116672 A3 | 11/2006 | | |
| WO | WO 2014/194334 A3 | 12/2014 | | |

OTHER PUBLICATIONS

Chang et al., "An efficient algorithm used for full-field optical coherence tomography", Optics and Lasers in Engineering, 2007, vol. 45, pp. 1170-1176.

Du, "Fast spatial carrier phase-shifting algorithm based on a constructed reference-phase", Optik, 2016, vol. 127, pp. 7829-7834.

Dubois, "Extended full-field optical coherence microscopy", International Topical Meeting on Optical Sensing and Artificial Vision, May 2012, Saint-Petersbourg, Russia, <hal-00713696>.

Dubois, "Full-Field Optical Coherence Microscopy", Gangjun Liu, Selected Topics in Optical Coherence Tomography, INTECH, 2012, pp. 3-20.

Min et al., "Numerical correction of distorted images in full-field optical coherence tomography", Meas. Sci. Technol., 2012, vol. 23, 9 pages, doi:10.1088/0957-0233/23/3/035403.

Subhash, "Full-Field and Single-Shot Full-Field Optical Coherence Tomography: A Novel Technique for Biomedical Imaging Applications", Hindawi Publishing Corporation, Advances in Optical Technologies, 2012, vol. 2012, Article ID 435408, 26 pages, doi:10.1155/2012/435408.

Tsai et al., "Ultrahigh-Resolution Optical Coherence Tomography with LED-Phosphor-Based Broadband Light Source", Applied Physics Express, 2013, vol. 6, pp. 122502-1 to 122502-4.

Xu et al., "A derivative method of phase retrieval based on two interferograms with an unknown phase shift", Optik, 2016, vol. 127, pp. 326-330.

Xu et al., "A new method of phase derivative extracting for off-axis quantitative phase imaging", Optics Communications, 2013, vol. 305, pp. 13-16.

Taiwanese Office Action and Search Report for Taiwanese Application No. 106127569, dated Mar. 13, 2018.

\* cited by examiner

INTERFEROMETER AND IMAGING METHOD THEREFOR

CROSS-REFERENCE TO RELATED ART

This application claims the benefit of a prior-filed U.S. provisional application Ser. No. 62/403,761, filed Oct. 4, 2016, and the benefit of Taiwan application Serial No. 106127569, filed Aug. 15, 2017, the subject matters of which are incorporated herein by references.

TECHNICAL FIELD

The disclosure relates in general to an interferometer and an imaging method therefor.

BACKGROUND

Optical coherence tomography (OCT) uses Michelson Interferometer and low coherence light source. Ideally, the light beam is split into two paths, a reference arm path and a sample arm path, by a beam splitter (BS). Light on the reference arm path is reflected by a planar mirror and a part of the reflected light from the planar mirror passes through the beam splitter and is incident onto a photodetector (PD). Light on the sample arm path is reflected by the test sample, and a part of the reflected light from the test sample is reflected by the beam splitter and is incident onto the photodetector. If light on the reference arm path and light on the sample arm path has overlap in coherence length, then they are interfered. The interference signal may be measured by the photodetector. The optical path difference (OPD) between the reference arm path and the sample arm path may be changed by moving the planar mirror forward and backward, to generate interference information of the test sample on different depth. The interference information may be further analyzed to obtain information of the test sample.

Full-field optical coherence tomography (FFOCT) is developed from a Time-domain OCT, which improved scanning and image capture of the traditional time-domain OCT to improve the scan speed.

SUMMARY

According to one embodiment, provided is an interferometer with demodulation function, used for inspecting a test sample. The interferometer includes: a light source being configured to provide a light beam; a beam splitting element being configured to receive and split the light beam from the light source into first incident light and second incident light, the first incident light being incident onto the test sample and reflected as first reflection light; a reflecting element being configured to receive the second incident light and reflect the second incident light as second reflection light; an optical detection element being configured to receive the first and the second reflect light to generate an interference signal; and a signal processing module coupled to the optical detection element, the signal processing module being configured to receive the interference signal and perform spatial differential calculation on the interference signal to generate a demodulation image of the test sample.

According to another embodiment, provided is an interferometer imaging method used for inspecting a test sample. The interferometer imaging method includes: providing a light beam; splitting the light beam into first incident light and second incident light; emitting the first incident light onto the test sample, wherein the first incident light is reflected as first reflection light; receiving the second incident light and reflecting the second incident light as second reflection light; receiving the first and the second reflect light to generate an interference signal; and receiving the interference signal and perform spatial differential calculation on the interference signal to generate a demodulation image of the test sample.

Figure 1:
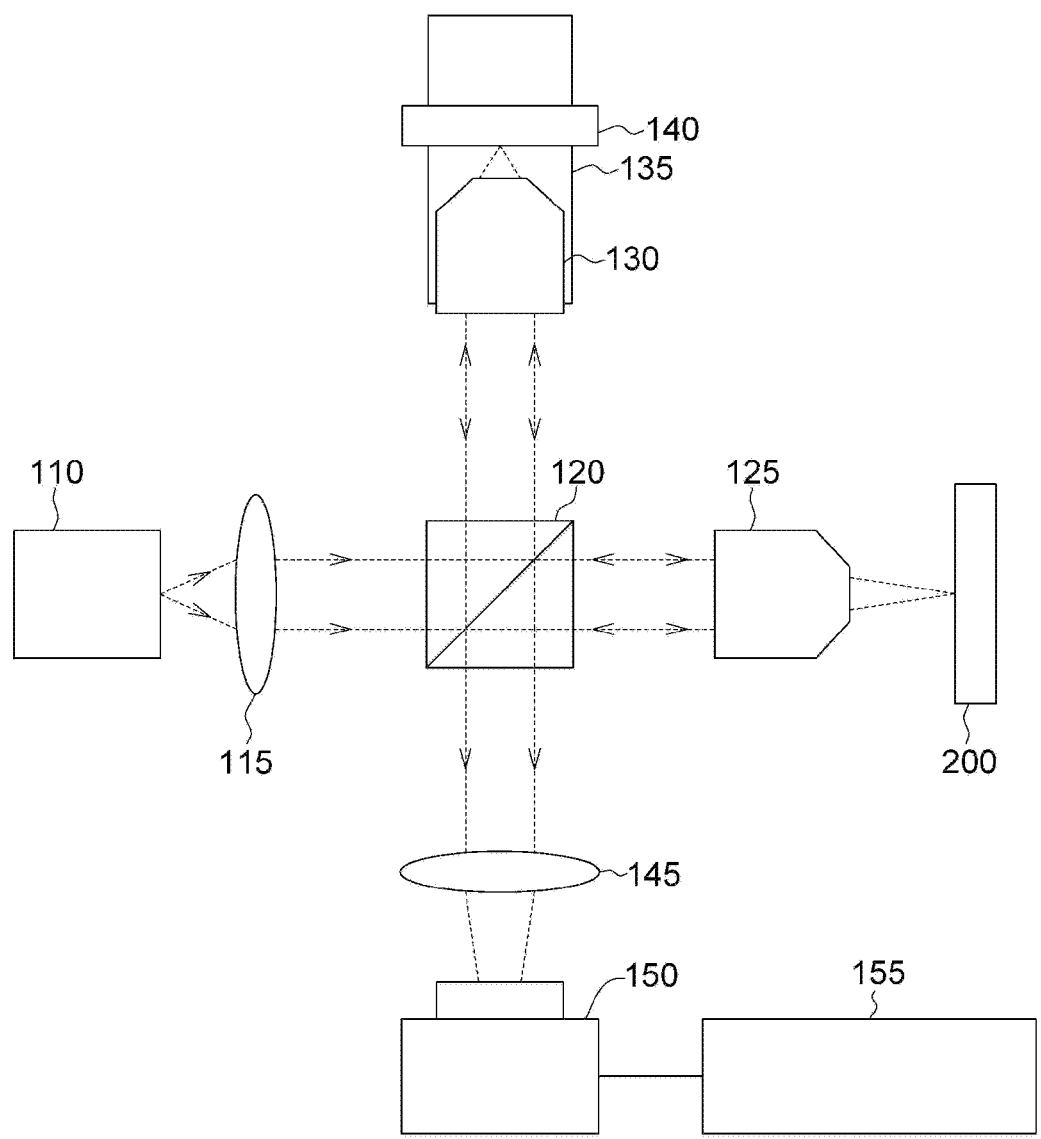
FIG. 1 is a structure diagram of an interferometer according to an embodiment of the application.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

DESCRIPTION OF THE EMBODIMENTS

Technical terms of the disclosure are based on general definition in the technical field of the disclosure. If the disclosure describes or explains one or some terms, definition of the terms is based on the description or explanation of the disclosure. Each of the disclosed embodiments has one or more technical features. In possible implementation, one skilled person in the art would selectively implement part or all technical features of any embodiment of the disclosure or selectively combine part or all technical features of the embodiments of the disclosure.

FIG. 1 is a structure diagram of an interferometer according to an embodiment of the application. As shown in FIG. 1, the interferometer 100 includes: a light source 110, a collimator lens 115, a beam splitting element (for example a beam splitter) 120, a test objective lens 125, a reference objective lens 130, a stepping motor stage 135, a reflecting element (for example, a reference mirror) 140, an imaging lens 145, an optical detection element 150 and a signal processing module 155. The interferometer 100 has a demodulation function for inspecting a test sample 200.

The light source 110 is configured for providing a light beam, for example a coherence light source/beam. The light beam from the light source 110 is incident on the collimator lens 115 to form a collimating parallel light.

The collimating parallel light from the collimator lens 115 is incident onto the beam splitting element 120 and split into two optical paths, a sample arm path and a reference arm path, by the beam splitting element 120. That is, the beam splitting element 120 receives the collimating parallel light and splits the collimating parallel light into first incident light and second incident light. The first incident light travels along the sample arm path and the second incident light travels along the reference arm path.

The test objective lens 125 is on the sample arm path. The test objective lens 125 focuses the first incident light onto the test sample 200. The first incident light focused by the test objective lens 125 is incident on the test sample 200 and is reflected as first reflection light.

The reference objective lens 130 is on the reference arm path. The reference objective lens 130 focuses the second incident light onto the reflecting element 140. The second incident light focused by the reference objective lens 130 is incident on the reflecting element 140. The reflecting element 140 reflects the second incident light as second reflection light.

The stepping motor stage 135 is configured to move the reflecting element 140 in steps, for adjusting an optical path difference (OPD) between the sample arm path and the reference arm path. By movement made by the stepping motor stage 135, images on the surface or images on different internal layers of the test sample 200 may be demodulated. Thus, the stepping motor stage 135 may be referred as depth scanning actuator.

The first reflection light reflected by the test sample 200 and the second reflection light reflected by the reflecting element 140 pass through the beam splitting element 120 and are focused by the imaging lens 145. The first and the second reflect light focused by the imaging lens 145 are incident onto the optical detection element 150.

The optical detection element 150 receives the first and the second reflect light to generate an interference signal (having interference fringe signal). The interference signal from the optical detection element 150 is sent to the signal processing module 155. The optical detection element 150 is for example but not limited by, an image sensor or CCD (Charge-coupled Device) or CMOS (Complementary Metal-Oxide-Semiconductor) image sensor. Of course, this is not to limit the application.

The signal processing module 155 is coupled to the optical detection element 150. The signal processing module 155 receives the interference signal and performs spatial differential calculation on the interference signal to generate a demodulation image of the test sample 200.

In details, the signal processing module 155 generates the demodulation image on a depth of the test sample 200 by a spatial differential algorithm. By controlling the movement of the stepping motor stage 135, the location of the reflecting element 140 may be adjusted for adjusting the optical path difference (OPD) between the sample arm path and the reference arm path to obtain the demodulation images on different depths of the test sample 200. In another possible embodiment of the application, the interferometer does not include the stepping motor stage 135 and thus, the interferometer may be configured to demodulate a demodulation image on a fixed depth of the test sample 200. That is, in demodulating the demodulation images at different or variable depths, the stepping motor stage 135 may be used to adjust the optical path difference (OPD) between the sample arm path and the reference arm path. However, in demodulating the demodulation image at a fixed depth, the interferometer does not include the stepping motor stage 135. These are still within the spirit and scope of the application.

Figure 2:
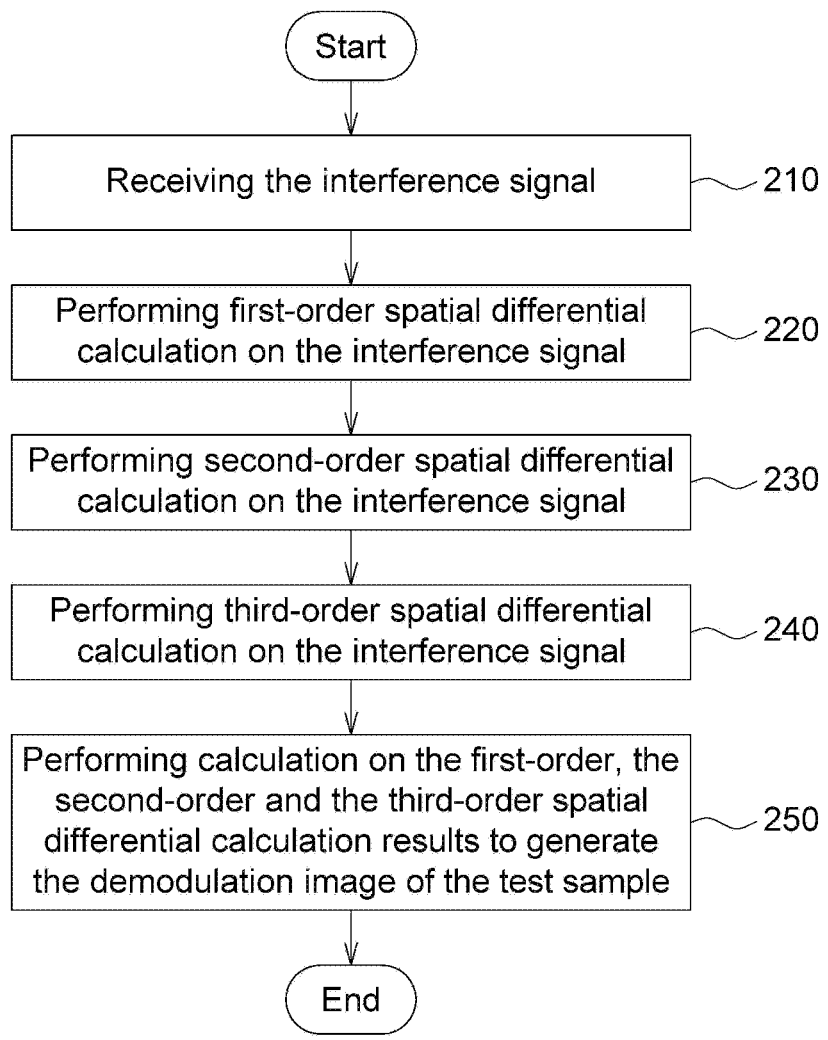
FIG. 2 is a demodulation flow chart according to an embodiment of the application.

FIG. 2 is a demodulation flow chart according to an embodiment of the application. FIG. 2 shows the steps in which the signal processing module 155 receives the interference signal and performs spatial differential calculation on the interference signal to generate the demodulation image of the test sample 200. In step 210, the signal processing module 155 receives the interference signal captured by the optical detection element 150. In step 220, the signal processing module 155 performs first-order spatial differential calculation on the interference signal. In step 230, the signal processing module 155 performs second-order spatial differential calculation on the interference signal. In step 240, the signal processing module 155 performs third-order spatial differential calculation on the interference signal. In step 250, the signal processing module 155 performs calculation on the first-order, the second-order and the third-order spatial differential calculation results obtained at steps 220-240 to generate the demodulation image of the test sample 200. The details of the steps 220-250 are described in the following.

Based on the interference theory, as for the spatial differential algorithm used in the embodiment of the application, the interference signal I(x,y) captured by the optical detection element 150 may be expressed as equation (1):

$$I(x,y)=I_{DC}(x,y)+A_i(x,y)\cos[\phi(x,y)+kx] \quad (1)$$

In equation (1), the term $I_{DC}(x,y)$ is a DC (direct current) background value (which represents the background light), the term $A_i(x,y)\cos[\phi(x,y)+kx]$ is an interference term (which represents the interference light signal), the term $A_i(x,y)$ is the amplitude of the "I"-th internal layer ("i" being a natural number) of scan image, the term $\phi(x,y)$ is the phase of the interference fringe and the term "k" is light wavenumber.

Performing x-differential calculation on the interference signal may be expressed as equation (2):

$$\frac{\partial I(x,y)}{\partial x} = \frac{\partial I_{DC}(x,y)}{\partial x} + \frac{\partial A_i(x,y)}{\partial x}\cos[\phi(x,y)+kx] - \quad (2)$$
$$A_i(x,y)\sin[\phi(x,y)+kx]\left[\frac{\partial \phi(x,y)}{\partial x}+k\right]$$

It is assumed that the background light (i.e. the first incident light from the beam splitting element 120) is uniformly and steadily incident on the test sample 200, then in equation (2), $$\frac{\partial I_{DC}(x,y)}{\partial x} \approx 0, \frac{\partial A_i(x,y)}{\partial x} \approx 0, \frac{\partial \phi(x,y)}{\partial x} \ll k.$$

In step 220, the signal processing module 155 performs the first-order spatial differential calculation on the interference signal and the result may be expressed in equation (3):

$$I'(x,y)=-kA_i(x,y)\sin[\phi(x,y)+kx] \quad (3)$$

In step 230, the signal processing module 155 performs the second-order spatial differential calculation on the interference signal and the result may be expressed in equation (4):

$$I''(x,y)=-k^2 A_i(x,y)\cos[\phi(x,y)+kx] \quad (4)$$

In step 240, the signal processing module 155 performs the third-order spatial differential calculation on the interference signal and the result may be expressed in equation (5):

$$I'''(x,y)=k^3 A_i(x,y)\sin[\phi(x,y)+kx] \quad (5)$$

By introducing trigonometric identity: $\sin^2\theta+\cos^2\theta=1$, the phase of the interference term in equations (3)-(5) may be removed and the result may be expressed in the equation (6):

$$A_i(x,y)=\sqrt{C((I'')^2-I'''\cdot I')} \quad (6)$$

In the equation (6), C is a constant value.

The above steps are for performing X-differential calculation, and the Y-differential calculation is performed similarly. In the embodiment of the application, if the interference image has variation on X-direction, then X-differential calculation is performed on the interference image. If the interference image has variation on Y-direction, then Y-differential calculation is performed on the interference image. If the interference image has variation on both X-direction and Y-direction, then both X-differential calculation and Y-differential calculation are performed on the interference image. In other words, the spatial differential calculation is related to the direction of the interference image. Besides, the "i" value in equations (1)-(6) refers to the scan image at different internal layers, and the "i" value may be changed by adjusting the stepping motor stage 135.

Figure 3:
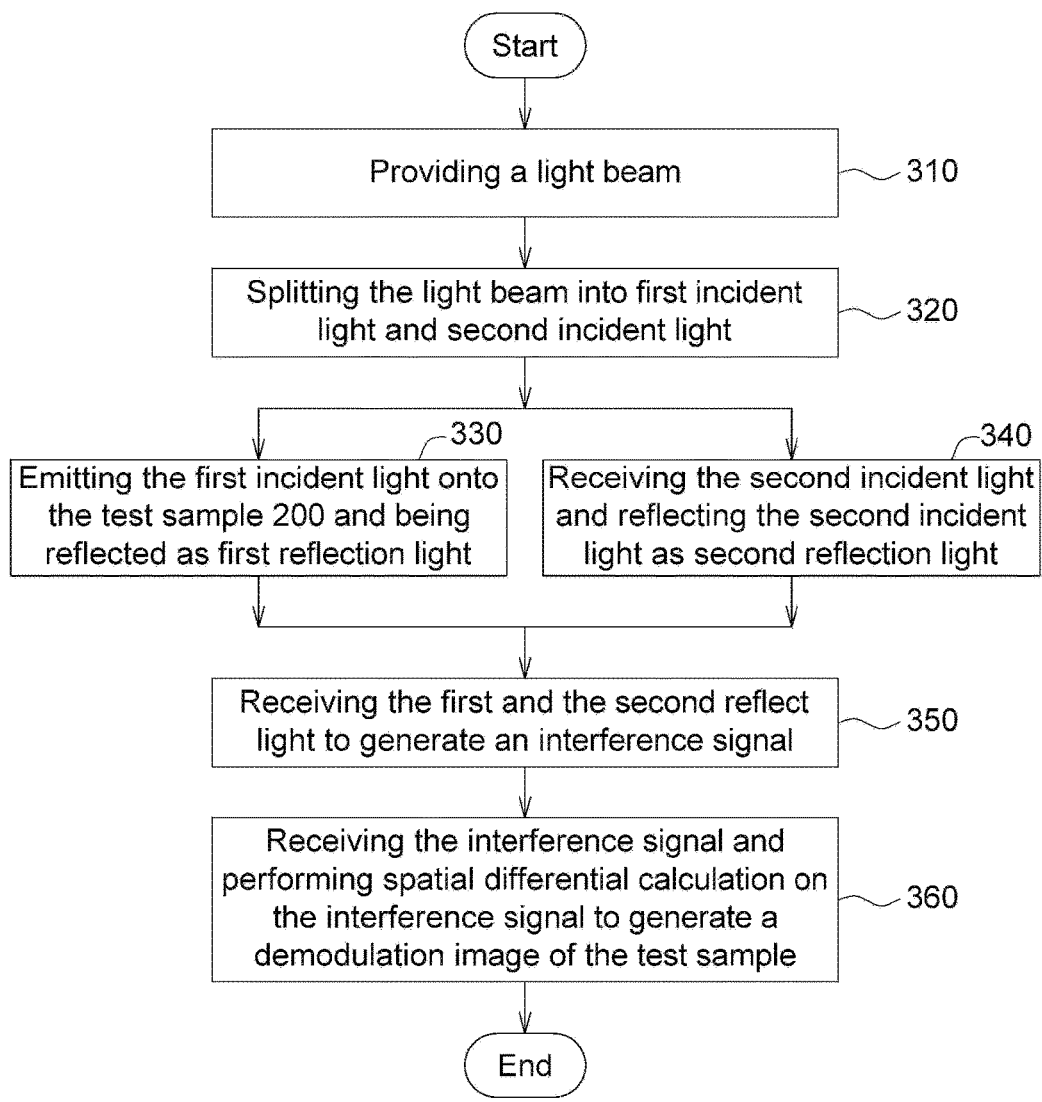
FIG. 3 is an imaging method of the interferometer according to an embodiment of the application.

FIG. 3 is an imaging method of the interferometer according to an embodiment of the application. In step 310, the light source provides a light beam. In step 320, the beam splitting element 120 receives and splits the light beam from the light source 110 into first incident light and second incident light. In step 330, the first incident light is directed by the test objective lens 125 onto the test sample 200 and is reflected as first reflection light. In step 340, the reflecting element 140 receives the second incident light and reflects the second incident light as second reflection light. In step 350, the optical detection element 150 receives the first and the second reflect light to generate an interference signal. In step 360, the signal processing module 155 receives the interference signal and performs spatial differential calculation on the interference signal to generate a demodulation image of the test sample 200.

In the embodiment of the application, by spatial differential calculation, the demodulation image of the test sample is obtained by using a single interference image. Therefore, the embodiment of the application may display the demodulation image of the test sample in real-time and thus has quick demodulation speed.

Further, in the embodiment of the application, because precise and expensive elements (for example PZT (Piezoelectric Transducer)) are eliminated, and thus the interferometer according to the embodiment of the application has low cost.

Further, the elements used in the interferometer according to the embodiment of the application have higher vibration resistance. For example, in tradition, the demodulation is performed by time differential. PZT is used in adjusting the location when the test sample is captured in different phase. However, the PZT has low vibration resistance. Thus, the traditional multi-image demodulation is easily influenced by vibration. On the contrary, the embodiment of the application performs demodulation by spatial differential calculation and it is enough to perform spatial differential calculation just based on a single image. Thus, no PZT is required in the interferometer according to the embodiment of the application. The interferometer according to the embodiment of the application will be not easily influenced by vibration, so the interferometer according to the embodiment of the application has higher vibration resistance.

It will be apparent to those skilled in the art that various modifications and variations can be made to the disclosed embodiments. It is intended that the specification and examples be considered as exemplary only, with a true scope of the disclosure being indicated by the following claims and their equivalents.

What is claimed is:

1. An interferometer with demodulation function, used for inspecting a test sample, the interferometer comprising:
a light source being configured to provide a light beam;
a beam splitter being configured to receive and split the light beam from the light source into first incident light and second incident light, the first incident light being incident onto the test sample and reflected as first reflection light;
a reference mirror being configured to receive the second incident light and reflect the second incident light as second reflection light;
an image sensor being configured to receive the first and the second reflection lights to generate an interference signal; and
a signal processor coupled to the image sensor, the signal processor being configured to receive the interference signal and perform spatial differential calculation on the interference signal to generate a demodulation image of the test sample, wherein the signal processor calculates $$\sqrt{C((I')^2 - I''' \cdot I)}$$

to generate the demodulation image, I referring the interference signal, I' being obtained by performing first-order spatial differential calculation on the interference signal, I'' being obtained by performing second-order spatial differential calculation on the interference signal, I''' being obtained by performing third-order spatial differential calculation on the interference signal and C being a constant value, wherein the spatial differential calculation consists of an X-differential calculation, a Y-differential calculation and a combined X-differential calculation and Y-differential calculation, and the signal processor is configured to perform the X-differential calculation when the interference signal has variation on an X-direction, perform the Y-differential calculation when the interference signal has variation on a Y-direction and perform the combined X-differential calculation and Y-differential calculation when the interference signal has variation on both the X-direction and the Y-direction.

2. The interferometer according to claim 1, further comprising:
a stepping motor stage being configured to move the reference mirror in steps, for adjusting an optical path difference (OPD) between a sample arm path and a reference axiii path to obtain a plurality of demodulation images on different internal layers of the test sample;
wherein the test sample is on the sample arm path and the reference mirror is on the reference arm path.

3. The interferometer according to claim 1, wherein the demodulation image of the test sample is obtained by using a single interference image.

4. An interferometer imaging method used for inspecting a test sample, the interferometer imaging method comprising:
providing a light beam;
splitting the light beam into first incident light and second incident light; emitting the first incident light onto the test sample, wherein the first incident light is reflected as first reflection light;
receiving the second incident light and reflecting the second incident light as second reflection light;
receiving the first and the second reflection lights to generate an interference signal;
and receiving the interference signal and performing spatial differential calculation on the interference signal to generate a demodulation image of the test sample,
wherein the step of performing spatial differential calculation on the interference signal to generate the demodulation image of the test sample comprises:

calculating $\sqrt{C((I'')^2 - I'''\cdot I')}$ to generate the demodulation image, I referring the interference signal, I' being obtained by performing first-order spatial differential calculation on the interference signal, I" being obtained by performing second-order spatial differential calculation on the interference signal, Y''' being obtained by performing third-order spatial differential calculation on the interference signal and C being a constant value, wherein the spatial differential calculation consists of an X-differential calculation, a Y-differential calculation and a combined X-differential calculation and Y-differential calculation, and the X-differential calculation is performed when the interference signal has variation on an X-direction, the Y-differential calculation is performed when the interference signal has variation on a Y-direction and the combined X-differential calculation and Y-differential calculation is performed when the interference signal has variation on both the X-direction and the Y-direction.

5. The interferometer imaging method according to claim 4, further comprising:
using a stepping motor stage to adjust an optical path difference (OPD) between a sample arm path and a reference arm path to obtain a plurality of demodulation images on different internal layers of the test sample.

6. The interferometer imaging method according to claim 4, wherein the demodulation image of the test sample is obtained by using a single interference image.

\* \* \* \* \*